(12) United States Patent
Casas

(10) Patent No.: US 10,881,768 B2
(45) Date of Patent: Jan. 5, 2021

(54) DRIVE LINE INFECTION PREVENTION USING A FLEXIBLE ARTIFICIAL SKIN ULTRA VIOLET (UV) LIGHT EMITTER

(71) Applicant: HeartWare, Inc., Miami Lakes, FL (US)

(72) Inventor: Fernando Casas, Miami Lakes, FL (US)

(73) Assignee: HeartWare, Inc., Miami Lakes, FL (US)

(*) Notice: Subject to any disclaimer, the term of this patent is extended or adjusted under 35 U.S.C. 154(b) by 168 days.

(21) Appl. No.: 16/131,340

(22) Filed: Sep. 14, 2018

(65) Prior Publication Data
US 2019/0091389 A1  Mar. 28, 2019

Related U.S. Application Data

(60) Provisional application No. 62/563,339, filed on Sep. 26, 2017.

(51) Int. Cl.
| | | |
|---|---|---|
| *A61M 1/10* | (2006.01) | |
| *A61M 1/12* | (2006.01) | |
| *A61L 2/10* | (2006.01) | |
| *A61L 2/00* | (2006.01) | |
| *A61L 2/26* | (2006.01) | |

(Continued)

(52) U.S. Cl.
CPC ......... *A61M 1/1008* (2014.02); *A61L 2/0047* (2013.01); *A61L 2/10* (2013.01); *A61L 2/26* (2013.01); *A61M 1/1086* (2013.01); *A61M 1/122* (2014.02); *A61N 5/0624* (2013.01); *A61L 2202/11* (2013.01); *A61L 2202/22* (2013.01); *A61L 2202/24* (2013.01); *A61M 2039/0285* (2013.01); *A61M 2039/167* (2013.01); *A61N 2005/0661* (2013.01)

(58) Field of Classification Search
CPC ........ A61M 2039/0285; A61M 1/1008; A61M 1/122; A61N 5/0624; A61L 2/0047; A61L 2/10
See application file for complete search history.

(56) References Cited

U.S. PATENT DOCUMENTS

2006/0259137 A1\* 11/2006 Artof ...................... A61F 2/243
623/2.18
2010/0204539 A1\* 8/2010 Tansley ................... A61M 1/12
600/17

(Continued)

FOREIGN PATENT DOCUMENTS

WO  2016187145 A1  11/2016

OTHER PUBLICATIONS

International Search Report and Written Opinion dated Dec. 4, 2018, for corresponding International Application No. PCT/US2018/051034; International Filing Date: Sep. 14, 2018 consisting of 10 pages.

*Primary Examiner* — Gary Jackson
*Assistant Examiner* — Zahed Kabir
(74) *Attorney, Agent, or Firm* — Christopher & Weisberg, P.A.

(57) ABSTRACT

A driveline for an implantable blood pump including a percutaneous outer tube configured to connect with the blood pump when the blood pump is implanted within a body of a patient and an external controller outside of the body of the patient and at least one ultra-violet light emitter coupled to the outer tube.

20 Claims, 3 Drawing Sheets

(51) Int. Cl.
*A61N 5/06* (2006.01)
*A61M 39/02* (2006.01)
*A61M 39/16* (2006.01)

(56) References Cited

U.S. PATENT DOCUMENTS

| | | | |
|---|---|---|---|
| 2011/0160516 A1* | 6/2011 | Dague | A61M 1/1086 600/16 |
| 2012/0203318 A1* | 8/2012 | Mann | A61M 39/0247 607/116 |
| 2015/0367049 A1* | 12/2015 | Chen | A61M 1/122 600/16 |
| 2016/0228061 A1* | 8/2016 | Kallback | A61B 5/01 |
| 2018/0200422 A1* | 7/2018 | Nguyen | A61M 1/122 |
| 2018/0289940 A1* | 10/2018 | Spotnitz | A61L 2/0047 |

* cited by examiner

DRIVE LINE INFECTION PREVENTION USING A FLEXIBLE ARTIFICIAL SKIN ULTRA VIOLET (UV) LIGHT EMITTER

CROSS-REFERENCE TO RELATED APPLICATION

This application claims the benefit of U.S. application Ser. No. 62/563,339, filed Sep. 26, 2017, the entirety of which is incorporated by reference herein.

FIELD

The present technology is generally related to a system and method for preventing tissue infection in patients with a driveline of an implantable blood pump.

BACKGROUND

The driveline of an implantable blood pump provides power from a blood pump disposed within a human or animal patient to an external power source, such as an external controller. The driveline is typically formed as an elongate tube containing one or more conductors that percutaneously extend through an opening in the patient's skin proximate the abdomen to connect with the blood pump. The patient should routinely wash and care for the opening to prevent infection, which can readily occur and create patient discomfort and/or necessitate removal and reinsertion of the driveline.

SUMMARY

The techniques of this disclosure generally relate to a driveline for an implantable blood pump including an ultra-violet light emitter coupled to the driveline.

In one aspect, the present disclosure provides a driveline for an implantable blood pump including a percutaneous outer tube configured to connect with the blood pump when the blood pump is implanted within a body of a patient and an external controller outside of the body of the patient and at least one ultra-violet light emitter coupled to the outer tube.

In another aspect, the disclosure provides the outer tube defining a lumen including one or more conductors disposed within the lumen and an exterior surface surrounding the lumen.

In another aspect, the disclosure provides the at least one ultra-violet light emitter being disposed around at least a portion of the exterior surface of the outer tube.

In another aspect, the disclosure provides a biocompatible fabric disposed around the exterior surface of the outer tube, and the at least one ultra-violet light emitter being coupled to the biocompatible fabric.

In another aspect, the disclosure provides the outer tube defining a circumference, and the at least one ultra-violet light emitter and the biocompatible fabric surround the circumference.

In another aspect, the disclosure provides the biocompatible fabric being a velour material.

In another aspect, the disclosure provides the biocompatible fabric including an interior surface and an exterior surface opposite the interior surface, the interior surface of the biocompatible fabric configured to be in contact with the exterior surface of the outer tube, and the at least one ultra-violet light emitter being disposed on the interior surface.

In another aspect, the disclosure provides the ultra-violet light emitter defining an ultra-violet light path through the biocompatible fabric and away from the outer tube.

In another aspect, the disclosure provides the outer tube defining a length and the at least one ultra-violet light emitter is selectively positioned along the length.

In another aspect, the disclosure provides the outer tube including a proximal portion and a distal portion opposite the proximal portion, the proximal portion being connected to the implantable blood pump when implanted in the body of the patient, and the distal portion extending through the body of the patient, and wherein at least one ultra-violet light emitter is disposed around the distal portion.

In another aspect, the disclosure provides the at least one ultra-violet light emitter being adhered to the outer tube.

In another aspect, the present disclosure provides a driveline for an implantable blood pump including a percutaneous outer tube coupled to the blood pump when the blood pump is implanted in a body of a patient, the outer tube defining a lumen including a plurality of conductors disposed therein and an ultra-violet light emitter contouring at least a portion of the outer tube and facing away from the outer tube.

In another aspect, the disclosure provides the outer tube defining a proximal portion and a distal portion opposite the proximal portion, the distal portion extending percutaneously away from the body of the patient and defining a skin interface when the blood pump is implanted in the body of the patient, and the ultra-violet light emitter is disposed at the skin interface of the distal portion of the outer tube.

In another aspect, the disclosure provides a biocompatible fabric including the ultra-violet light emitter in contact therewith.

In another aspect, the disclosure provides the biocompatible fabric including an interior surface and an exterior surface opposite the interior surface, the interior surface of the biocompatible fabric being in contact with the outer tube and including the ultra-violet light emitter disposed thereon.

In another aspect, the disclosure provides the biocompatible fabric being a velour material.

In another aspect, the disclosure provides the ultra-violet light emitter being adhered to the outer tube.

In another aspect, the disclosure provides the ultra-violet light emitter being made of a flexible material.

In another aspect, the disclosure provides the ultra-violet light emitter surrounding the outer tube and defining an ultra-violet light path projecting away from the outer tube.

In another aspect, the disclosure provides a driveline for an implantable blood pump including a percutaneous outer tube having a proximal portion and a distal portion opposite the proximal portion, the proximal portion being couplable to the blood pump when implanted within a body of a patient and the distal portion being couplable to an external controller outside of the body of the patient, the outer tube defining a lumen including a plurality of conductors disposed therein and an exterior surface surrounding the lumen. In addition, the driveline includes a biocompatible fabric in contact with the outer tube at the distal portion of the outer tube, the biocompatible fabric including an interior surface and an exterior surface opposite the interior surface and at least one ultra-violet light emitter disposed between the interior surface of the biocompatible fabric and the exterior surface of the outer tube.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of embodiments described herein, and the attendant advantages and features thereof, will be more readily understood by reference to the following detailed description when considered in conjunction with the accompanying drawings wherein.

DETAILED DESCRIPTION

Figure 1:
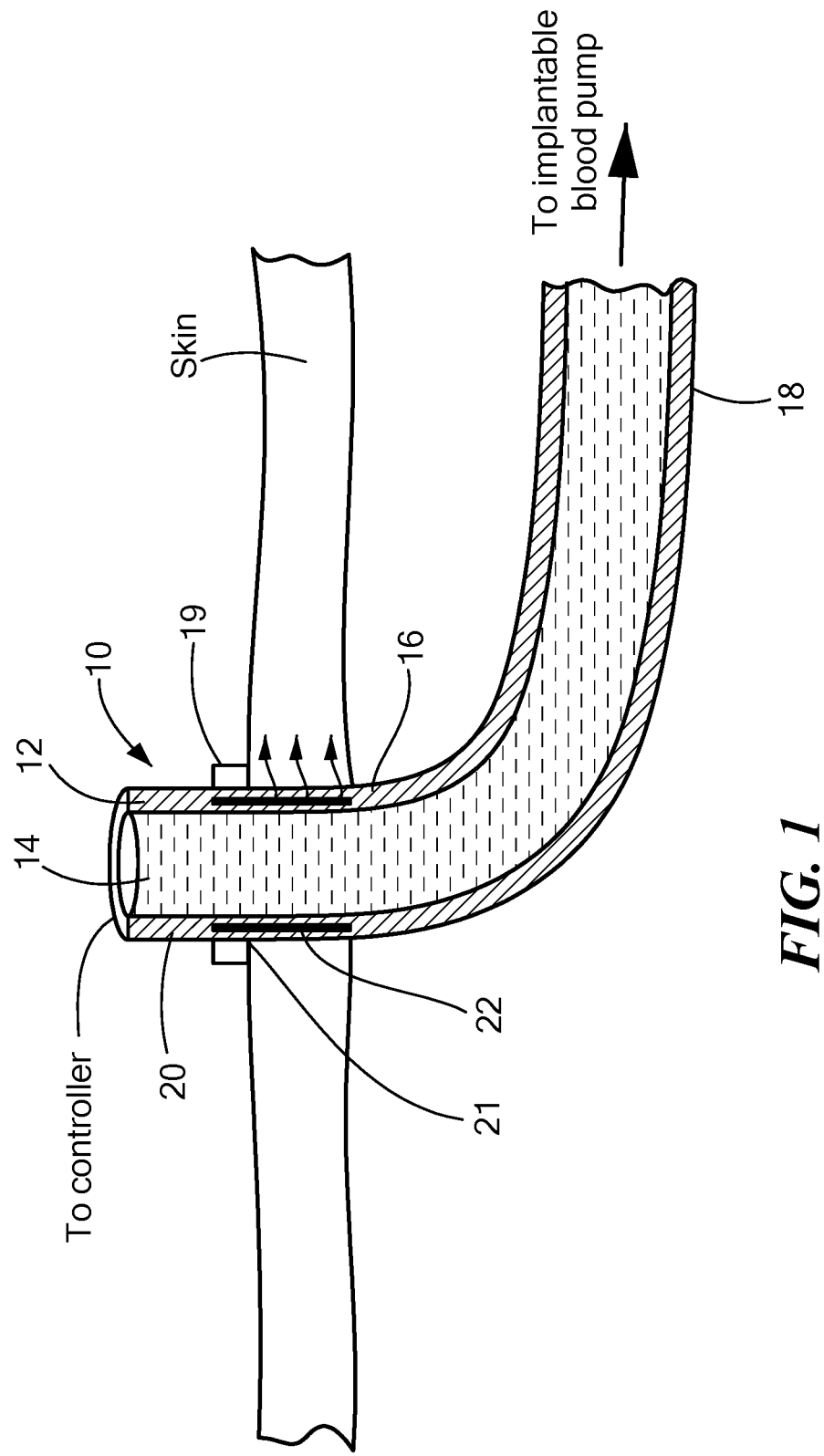
FIG. 1 is a cross-sectional view of an exemplary driveline extending through the skin of a patient and connectable to an implantable blood pump, the driveline including a biocompatible fabric and an ultra-violet light emitter coupled thereto.

Before describing in detail exemplary embodiments, it is noted that the embodiments reside primarily in combinations of system and processing steps related to a driveline for an implantable blood pump including an ultra-violet light emitter coupled thereto. Accordingly, the system and process components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described processes or methods may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 2:
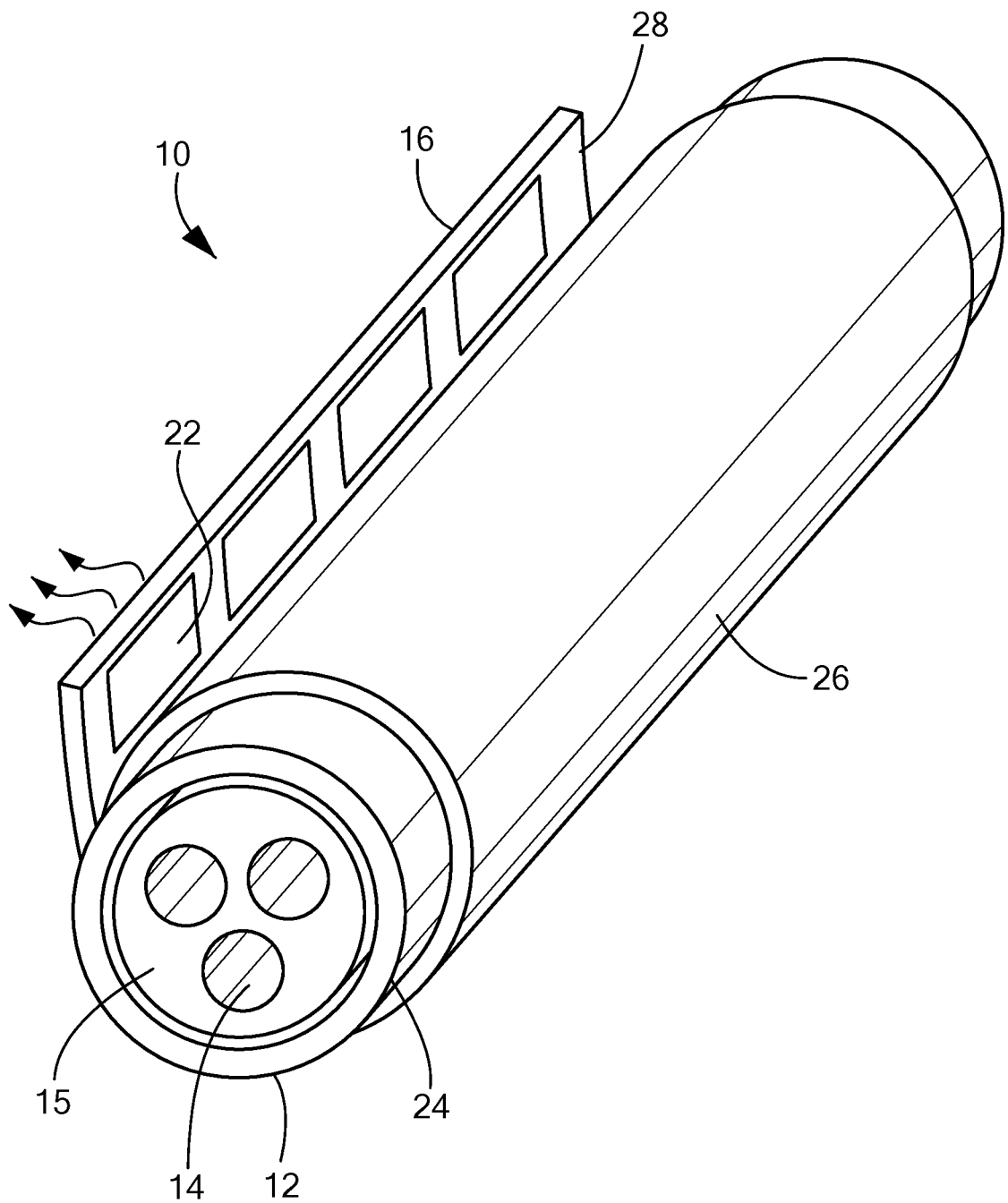
FIG. 2 is a perspective view of the driveline of FIG. 1.
Figure 3:
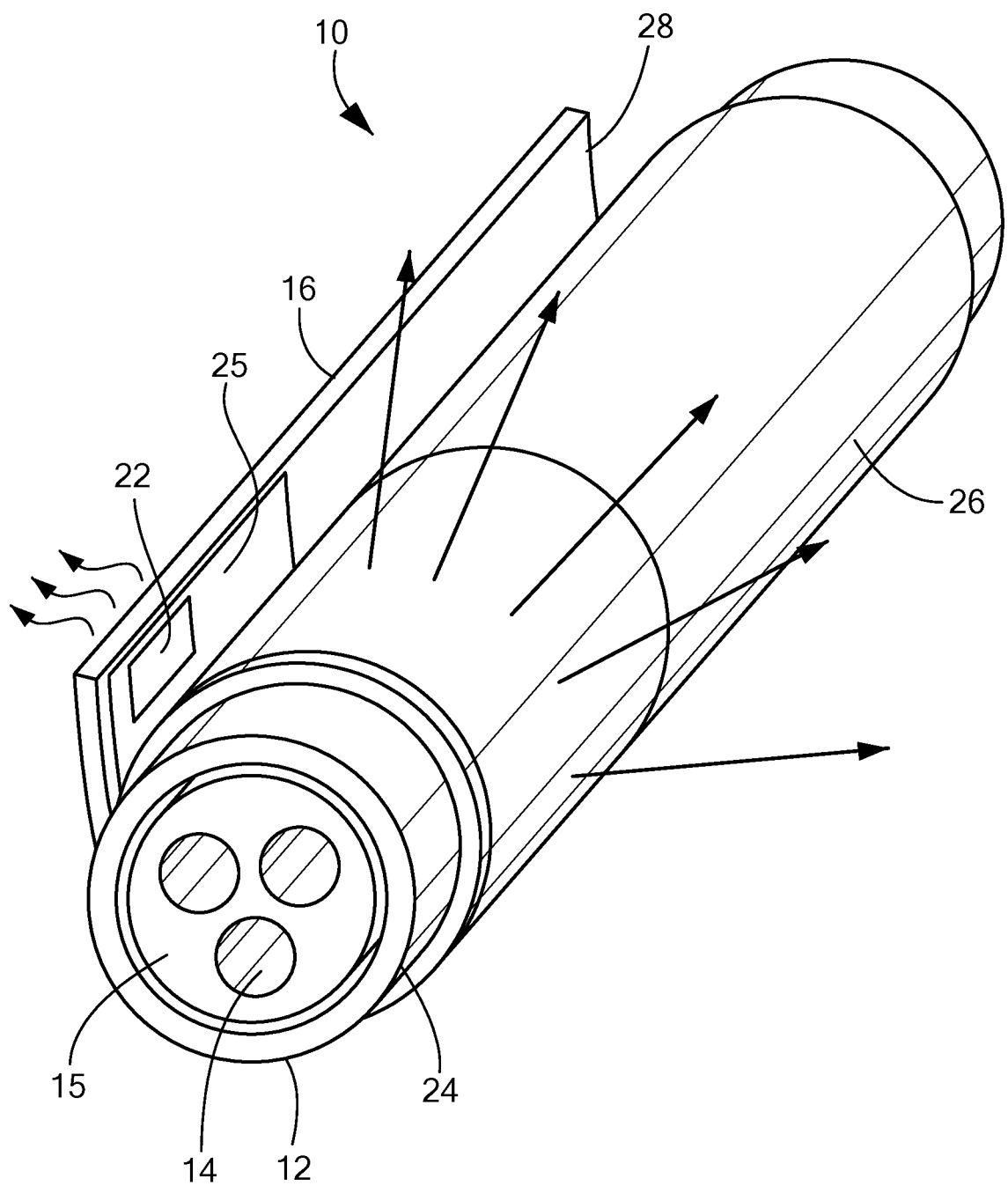
FIG. 3 is a perspective view of the driveline of FIG. 1 showing the ultra-violet light emitter extending around a circumference of the driveline.

Referring now to the drawings in which like reference designators refer to like elements, there is shown in FIGS. 1-3 an exemplary driveline constructed in accordance with the principles of the present disclosure and designated generally as "10." The driveline 10 may be made of a flexible material that extends a predetermined length from an implanted blood pump coupled to heart of a human or an animal patient percutaneously out of the patient at the abdomen. As such, when implanted, the driveline 10 includes a percutaneous connector which extends through the skin such that the driveline 10 connects the implanted blood pump to a device external to the patient, such as an external controller, to define a communication channel between the blood pump and the external controller.

With reference to FIG. 1, the driveline 10, includes an outer tube 12 defining at least one lumen 14 for receiving a conductor therethrough. The outer tube 12 may be composed of a flexible, biocompatible, and water proof material, for example, nylon, braided nylon, or the like, which may incorporate material properties configured to prevent kinking. FIG. 2 depicts the outer tube 12 defining three lumens 14 for receiving corresponding conductors therein, however more or less lumens may be provided. The lumens 14 may further be formed by or disposed within an inner tube 15 that spans all or a majority of the length of the outer tube 12 to insulate the conductors. The inner tube 15 may be slidable within an inner diameter of the outer tube 12 or otherwise disposed within the outer tube 12.

With reference to FIGS. 1 and 2, a biocompatible fabric 16 may be coupled to the outer tube 12 to promote tissue ingrowth into the driveline 10. In one configuration, the fabric 16 is a velour material. In other configurations, the fabric 16 may be a woven polyester or another fabric that is biocompatible and prone to promoting tissue ingrowth. The fabric 16 may be wrapped around the outer tube 12 and extend the entire length or less than the entire length of the outer tube 12. For example, as shown in FIG. 1, the outer tube 12 defines a proximal portion 18 and a distal portion 20 opposite the proximal portion 18. When the driveline 10 is implanted in the body of the patient, the proximal portion 18 of the outer tube 12 may be connected to an implantable blood pump (not shown) and the distal portion 20 may extend percutaneously to couple to an external controller (not shown). The distal portion 20 may include the percutaneous connector 19 and the portion of the outer tube 12 extending to a midpoint of the outer tube 12 along the length. The distal portion 20 defines a skin interface 21 at the location where the outer tube 12 exits the skin of the patient. In one configuration, the fabric 16 is wrapped around or otherwise coupled to only the distal portion 20 of the outer tube 12.

At least one ultra-violet light emitter 22 may be permanently or releasably coupled to the fabric 16 or the driveline 10 independent of the fabric 16. The number of ultra-violet light emitters 22 may vary and reference to the ultra-violet light emitter 22 in the singular is intended to encompass one or more ultra-violet light emitters 22. The ultra-violet light emitter 22 emits ultra-violet light which acts as a disinfectant to sterilize the driveline 10, prevent infection, and/or prevent inflammation along the driveline 10, such as around the skin interface 21, i.e., exit site through the patient's skin. The ultra-violet spectrum emitted from the ultra-violet light emitter 22 may be controlled by an external processor, such as a processor in the external controller (not shown). The external processor may also control the selective activation, duration, and shutdown of the ultra-violet light from one or more of the ultra-violet light emitters 22 individually or in select combinations in collaboration with one or more switches or circuits in communication with the external processor.

The ultra-violet light emitter 22 may be coupled to the driveline 10 in various configurations. For example, the ultra-violet light emitter 22 may be printed onto the outer tube 12 through a printing process, coupled to the outer tube 12 using an adhesive, or clamped or otherwise mechanically coupled to the outer tube 12. In other configurations, the ultra-violet light emitter 22 may be affixed, adhered to, or embedded within the fabric 16.

FIG. 1 depicts the ultra-violet light emitter 22 embedded within the fabric 16 and contouring the outer tube 12. The fabric 16 and one or more ultra-violet light emitters 22 may be located along one or more select portions of the length of the outer tube 12. For example, FIG. 1 depicts the ultra-violet light emitter 22 at the distal portion 20 of the outer tube 12 at the skin interface 21 to disinfect the skin interface 21 which may be subject to a relatively higher risk of infection in comparison to the remaining portions of the outer tube 12. In other configurations, the fabric 16 and the ultra-violet light emitter 22 may extend an entire length of the outer tube 12 or select portions along the length.

For example, FIG. 2 depicts the fabric 16 and four ultra-violet light emitters 22 extend along the length, although the quantity may vary.

In addition, the outer tube 12 includes an exterior surface 24 which defines the circumference of the outer tube 12 and the fabric 16 may be wrapped around a portion of the circumference including the entire or less than the entire circumference. The fabric 16 defines an exterior surface 26 and an interior surface 28 opposite the exterior surface 26. The ultra-violet light emitter 22 may be adhered to or embedded on the interior surface 28 to isolate the ultra-violet light emitter 22 from moisture and fluids, while allowing UV light emitted from the ultra-violet light emitter 22 to penetrate through the exterior surface 26 of the fabric 16 away from the outer tube 12. In other words, the interior surface 28 of the fabric 16 may overlap the exterior surface 26 of the fabric 16 to fluidically seal the ultra-violet light emitter 22 therebetween. In other configurations, the ultra-violet light emitter 22 may be coupled directly to the exterior surface 24 of the outer tube 12. The emitted ultra-violet spectrum may be selected and/or altered, such as by the external controller, to minimize or eliminate spectral interference from the fabric 16, thus optimizing the effect of the ultra-violet light.

FIG. 3 depicts the fabric 16 and the ultra-violet light emitter 22 incorporated as part of a MEMS device 25 that is coupled to or integrated within the driveline 10. For example, the MEMS device 25 may be a flexible circuit sticker having circuitry configured to receive power and supply such power to the ultra-violet light emitter 22. The power may be received by way of passive inductive radiofrequency charging, transcutaneous energy harvesting, a separate transcutaneous energy transfer system, or other methods known in the art. In one configuration, the separate transcutaneous energy transfer system may be coupled to the external processor and used to power the ultra-violet light emitter 22 during select times, such as at night. Alternatively, one or more of the conductors disposed within the driveline 10 may be split or a separate conductor may be included in the driveline 10 to power the ultra-violet light emitter 22. As show in FIG. 3, the ultra-violet light emitter 22 may be wrapped around the outer tube 12 to define a 360-degree circle of emitted ultra-violet light projecting away from the outer tube 12 to disinfect or treat the driveline 10. For example, the ultra-violet light emitter 22 may be wrapped around the circumference of the outer tube 12, such as at the skin interface 21 of the driveline 10, as part of the MEMS device 25 or otherwise coupled to the fabric 16 to emit the ultra-violet light.

It will be appreciated by persons skilled in the art that the present disclosure is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the disclosure, which is limited only by the following claims.

What is claimed is:

1. A driveline for an implantable blood pump, comprising:
   a percutaneous outer tube configured to connect with the blood pump when the blood pump is implanted within a body of a patient and an external controller outside of the body of the patient; and
   at least one ultra-violet light emitter coupled to the outer tube as part of a MEMS device, wherein the MEMS device having circuitry configured to power the at least one ultra-violet light emitter by inductive radiofrequency charging.

2. The driveline of claim 1, wherein the outer tube defines a lumen including a plurality of conductors disposed within the lumen and an exterior surface surrounding the lumen.

3. The driveline of claim 2, wherein the at least one ultra-violet light emitter is disposed around at least a portion of the exterior surface of the outer tube.

4. The driveline of claim 3, further including a biocompatible fabric disposed around the exterior surface of the outer tube, and the at least one ultra-violet light emitter being coupled to the biocompatible fabric.

5. The driveline of claim 4, wherein the outer tube defines a circumference, and the at least one ultra-violet light emitter and the biocompatible fabric surround the circumference.

6. The driveline of claim 5, wherein the biocompatible fabric is a velour material.

7. The driveline of claim 6, wherein the biocompatible fabric includes an interior surface and an exterior surface opposite the interior surface, the interior surface of the biocompatible fabric configured to be in contact with the exterior surface of the outer tube, and the at least one ultra-violet light emitter being disposed on the interior surface.

8. The driveline of claim 7, wherein the ultra-violet light emitter defines an ultra-violet light path through the biocompatible fabric and away from the outer tube.

9. The driveline of claim 1, wherein the outer tube defines a length and the at least one ultra-violet light emitter is selectively positioned along the length.

10. The driveline of claim 1, wherein the outer tube includes a proximal portion and a distal portion opposite the proximal portion, the proximal portion being connected to the implantable blood pump when implanted in the body of the patient, and the distal portion extending through the body of the patient and defining a skin interface, and wherein at least one ultra-violet light emitter is disposed around the skin interface.

11. The driveline of claim 1, wherein the at least one ultra-violet light emitter is adhered to the outer tube.

12. A driveline for an implantable blood pump, comprising:
    a percutaneous outer tube coupled to the blood pump when the blood pump is implanted in a body of a patient, the outer tube defining a lumen including a plurality of conductors disposed therein; and
    an ultra-violet light emitter as part of a MEMS device contouring at least a portion of the outer tube and facing away from the outer tube, wherein the MEMS device having circuitry configured to power the at least one ultra-violet light emitter by inductive radiofrequency charging.

13. The driveline of claim 12, wherein the outer tube defines a proximal portion and a distal portion opposite the proximal portion, the distal portion extending percutaneously away from the body of the patient and defining a skin interface when the blood pump is implanted in the body of the patient, and the ultra-violet light emitter is disposed at the skin interface of the distal portion of the outer tube.

14. The driveline of claim 12, further comprising a biocompatible fabric including the ultra-violet light emitter in contact therewith.

15. The driveline of claim 14, wherein the biocompatible fabric includes an interior surface and an exterior surface opposite the interior surface, the interior surface of the biocompatible fabric being in contact with the outer tube and including the ultra-violet light emitter disposed thereon.

16. The driveline of claim 15, wherein the biocompatible fabric is a velour material.

17. The driveline of claim 12, wherein the ultra-violet light emitter is adhered to the outer tube.

18. The driveline of claim 12, wherein the ultra-violet light emitter is made of a flexible material.

19. The driveline of claim 12, wherein the ultra-violet light emitter surrounds the outer tube and defines an ultra-violet light path projecting away from the outer tube.

20. A driveline for an implantable blood pump, comprising:
    a percutaneous outer tube including a proximal portion and a distal portion opposite the proximal portion, the proximal portion being couplable to the blood pump when implanted within a body of a patient and the distal portion being couplable to an external controller outside of the body of the patient, the outer tube defining a lumen including a plurality of conductors disposed therein and an exterior surface surrounding the lumen;
    a biocompatible fabric in contact with the outer tube at the distal portion of the outer tube, the biocompatible fabric including an interior surface and an exterior surface opposite the interior surface; and
    at least one ultra-violet light emitter as part of a MEMS device disposed between the interior surface of the biocompatible fabric and the exterior surface of the outer tube, wherein the MEMS device having circuitry configured to power the at least one ultra-violet light emitter by inductive radiofrequency charging.

* * * * *